Figure 1:
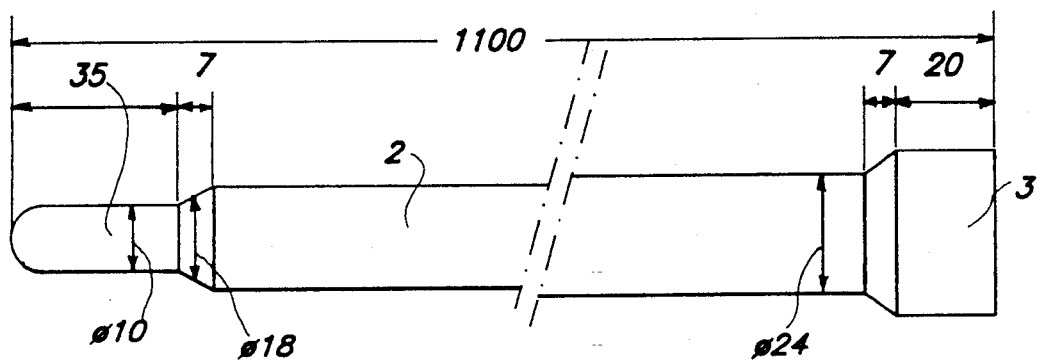

United States Patent [19]

Stolk

[11] Patent Number: 5,088,178

[45] Date of Patent: Feb. 18, 1992

[54] ULTRASONIC ENDOSCOPE PROVIDED WITH PROTECTIVE SHEATH

[75] Inventor: Albert F. Stolk, Moerkapelle, Netherlands

[73] Assignee: bv Optische Industrie, Delft, Netherlands

[21] Appl. No.: 449,885

[22] PCT Filed: Jul. 12, 1988

[86] PCT No.: PCT/EP88/00629

§ 371 Date: Dec. 20, 1989

§ 102(e) Date: Dec. 20, 1989

[87] PCT Pub. No.: WO89/00832

PCT Pub. Date: Feb. 9, 1989

[30] Foreign Application Priority Data

Jul. 27, 1987 [NL] Netherlands .................... 8701770

[51] Int. Cl.$^5$ ............... B23P 11/02; A61B 1/00
[52] U.S. Cl. ........................ 29/453; 29/448; 128/4
[58] Field of Search .............. 128/4, 6, 7, 23; 29/448, 453, 728, 235; 604/349

[56] References Cited

U.S. PATENT DOCUMENTS

| | | | |
|---|---|---|---|
| 2,670,736 | 3/1954 | Dunkelberger | 29/235 X |
| 2,696,209 | 12/1954 | Varaney | 128/132 |
| 3,866,601 | 2/1975 | Russell | 128/4 |
| 4,368,894 | 1/1983 | Parmann | 29/453 X |
| 4,593,699 | 6/1986 | Poncy et al. | 128/660 |
| 4,646,722 | 3/1987 | Silverstein et al. | 128/4 |
| 4,741,326 | 5/1988 | Sidall et al. | 128/4 |
| 4,821,398 | 4/1989 | Hillstead | 29/235 X |

FOREIGN PATENT DOCUMENTS 1541390 7/1977 United Kingdom .

Primary Examiner—Joseph M. Gorski
Assistant Examiner—S. Thomas Hughes
Attorney, Agent, or Firm—Louis E. Marn

[57] ABSTRACT

A method and device are described for fitting a flexible elongated thin-walled protective sheath around the head and tranmission tube of an ultrasonic endoscope. First, the protective sheath is slid onto the nozzle section of a fitting funnel in a gathered condition. The head and transmission tube are then fitted into the protective sheath via the mouth of the fitting funnel. By moving the fitting funnel along the transmission tube, the protective sheath is pulled taut over the head and the transmission tube.

7 Claims, 1 Drawing Sheet

ULTRASONIC ENDOSCOPE PROVIDED WITH PROTECTIVE SHEATH

The invention relates to a method and device for fitting a flexible elongated thin-walled protective tube around a head used for diagnostic purposes and an elongated transmission tube joined thereto for transmitting image signals originating from the head.

Such a method and device, as well as a protective tube to be used therewith, are known from the U.S. Pat. No. 4,646,722.

According to a method known therefrom, the open end of a protective tube to be fitted is attached in an airtight sealing manner to an annular seating of an inflating sleeve. Said sleeve is provided with a connecting nipple via which blower air can be fed to the interior of the sleeve and the protective tube attached thereto. Said sleeve is also provided with an annular sealing element fitted therein which is intended to enclose in an airtight sealing manner the transmission tube which is joined to the diagnostic head.

After said sleeve has been fitted at the end where said diagnostic head is located, i.e. around the transmission tube, air is fed via the connecting nipple, as a result of which the protective tube attached to the sleeve is inflated. As a result of this it is possible to pull the sleeve and the protective tube over the transmission tube, the sealing element of the sleeve being slid over the outer surface of the transmission tube. Once said transmission tube is surrounded by the expanded protective tube over the desired length, it is arranged that the air is able to escape, as a result of which the protective tube encloses, in a close fitting manner, the transmission tube and the diagnostic head joined thereto.

This known technique is laborious and time-consuming. In addition, it is a requirement that a source of compressed air is available. Viewed from a factory engineering viewpoint it is also unattractive for the sleeve to have to continue simultaneously to form an airtight seal in this process while being slid over the transmission tube.

The object of the invention is to meet the drawbacks outlined above.

For this purpose a method according to the invention is characterized by the following steps:

a) with the exception of a relatively short and sealed end section, the protective tube is slid onto the nozzle section of a fitting funnel in a manner such that the protective tube is situated on said nozzle section in a gathered condition;

b) the head and the section of the transmission tube joined thereto is fitted therein via the enlarged section of the fitting funnel and displaced with respect thereto in a manner such that said head is situated in the protective tube and has reached the said end section of the protective tube; and c) the transmission tube is held in position while the fitting funnel and the section of the protective tube present thereon are moved over the transmission tube until said protective tube has assumed the stretched condition.

A method proposed by the invention makes it possible to effect a pertinent assembly of diagnostic head and transmission tube in a protective tube in an efficient and simple manner.

The method according to the invention can be used with advantage in those cases in which the head used for diagnostic purposes is an ultrasound transducer. In this case it is necessary for such a transducer to be acousticly coupled to a transmission medium which conducts ultrasound well. For this purpose use is generally made of a transmission gel. Since such a gel has a certain lubricating action, it is necessary, in view of a required facility to rotate the transducer around the longitudinal axis of the transmission tube, that only the transducer is in contact with gel so that no transmission gel is present between the inside wall of the protective tube and the outer surface of the transmission tube.

A method suitable for the above-mentioned use is, according to the invention, characterized in that, after the step in which, with the exception of a relatively short and sealed end section, the protective tube is slid onto the nozzle section of a fitting funnel in a manner such that said protective tube is situated on said nozzle section in a gathered condition, and prior to the step in which the transducer and the section of the transmission tube connected thereto are fitted therein via the enlarged section of the fitting funnel and are displaced with respect thereto in a manner such that said head is situated in the protective tube and has reached the said end section, a certain quantity of transmission medium which conducts ultrasound well is injected into the said end section of the protective tube via the enlarged section of the fitting funnel; and the transducer is displaced in the protective tube in a manner such that said transducer is acoustically coupled to the injected transmission medium.

As is reported in the above-mentioned U.S. Pat. No. 4,646,722, an assembly of diagnostic head and transmission tube is often used in combination with an operating case from which, inter alia, the doctor in attendance can manipulate the transducer. It is usual to cause such an operating case to be connected to said transmission tube on the side facing the transmission tube via a conically sloping section. Within the framework of the invention a detachable snap coupling may be achieved between the fitting funnel and the operating case in a simple manner.

In view of this, the method according to the invention is characterized in that the end section of the protective tube situated on the fitting funnel is splayed out around the rim of the enlarged funnel section.

After use, the fitting funnel with the section of the protective tube splayed out around it can be decoupled from the operating case in a simple manner, it being possible to remove said funnel and the protective tube from the transmission tube and transducer. After this the protective tube is detached from the funnel nozzle and thrown away.

A device used for applying a method according to the invention is characterized, according to the invention, by a fitting funnel which is capable of allowing through a pertinent diagnostic head; and is further characterized in that the outside dimensioning of the nozzle section of the fitting funnel and the inside dimensioning of the protective tube are matched to each other in a manner such that the protective tube, regarded up to the end of the said end section, can be slid over the nozzle section; and the length of the nozzle section is short in comparison with the length of the pertinent transmission tube.

A protective tube to be used in a method according to the invention is, according to the invention, characterized by a segment, adjoining the open end section of the protective tube whose passage cross sections, regarded over the length of said segment, are smaller than the passage cross sections regarded over the length of the said open end section; and each passage cross section of the said segment is larger than the maximum contour cross section of the nozzle section of the fitting funnel.

Such a protective tube, when it has to be used in combination with an ultrasound transducer, is characterized, according to the invention, in that the said relatively short and sealed end section of the protective tube has internal cross sections, viewed over virtually the whole length of said end section, which are each smaller than the passage cross sections of said segment.

Figure 2:
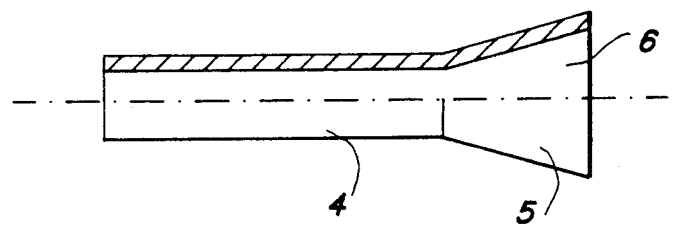
Figure 3:
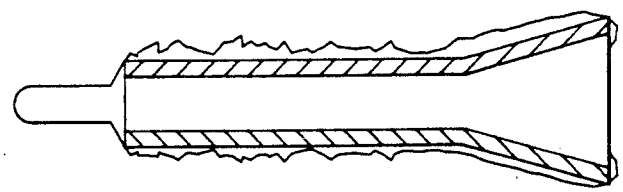
Figure 4:
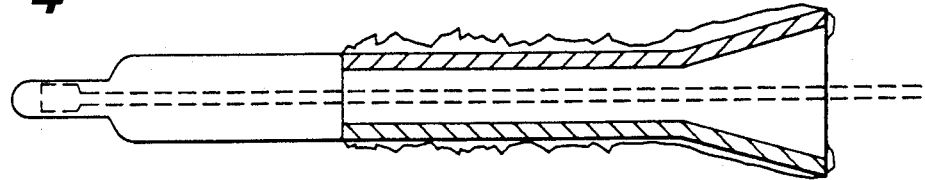

The invention will be explained in more detail below with reference to the drawing, wherein:

FIG. 1 gives a view of an illustrative exemplary embodiment of a protective tube to be used within the framework of the invention;

FIG. 2 shows an embodiment, portrayed partially in section and partially in view, of a fitting funnel used for applying the method according to the invention;

FIG. 3 portrays diagrammatically the situation in which, during the implementation of the method according to the invention, a protective tube of the type portrayed in FIG. 1 is fitted in the gathered condition on the nozzle section of the fitting funnel of the type portrayed in FIG. 2;

FIG. 4 portrays diagrammatically the situation in which, as a further phase of the method according to the invention, a section of the protective tube is pulled off the nozzle section of the fitting funnel and is brought to the stretched condition.

Without being limited thereto, the invention will be explained in more detail below by a description of an exemplary embodiment in which an ultrasound transducer and a transmission tube joined thereto have to be fitted in the interior of a protective tube.

In this connection, various types of transducer are usual such as, for example, a transducer having, for example, 64 elements, which depending on the control electronics, can cause an image to be displayed of an object to be investigated within a sector-shaped frame or within a rectangular frame.

According to a conceived application, such a transducer is used to form, from the oesophagus, images of the heart, which is located in the vicinity thereof, or other organs, or to form images of other organs from other openings in the body.

Before it is possible to introduce the assembly of transducer and transmission tube into the oesophagus, it is necessary to fit said assembly in the interior of a protective tube. This is a flexible thin-walled tube which is open at the one end and closed at the other end and which, for example, is manufactured from latex rubber. In FIG. 1, shape and dimensions are shown which are illustrative of such a protective tube.

The exemplary embodiment of a protective tube portrayed in FIG. 1 comprises a reservoir segment 1, an intermediate segment 2 and a feed segment 3. It is the intention that the transducer is finally situated in the reservoir segment and is surrounded there by an acoustic transmission gel, while the transmission tube via which the image signals formed by the transducer are removed extends through the interior of the intermediate segment 2 and the feed segment 3 to an operating case (not shown). Attention is drawn to the fact that use is usually made of a transducer whose working region is directed transversely with relation to the longitudinal axis of the transmission tube. At the same time, it should be possible for the transducer to be rotated around said longitudinal axis in order to be able to observe a pertinent organ, such as, for example, the heart, from various angles. In view of this, it is necessary for no transmission gel to be present between the inside wall of the intermediate segment 2 and the outer surface of the transmission tube extending through the interior of said segment. After all, only then is it possible to rotate the transmission tube and, consequently, the transducer about the longitudinal axis by means of a section of the intermediate segment situated outside the patient.

In order to carry out the method according to the invention use should be made of a fitting funnel.

An exemplary embodiment illustrative of this is shown in FIG. 2. Such a funnel comprises a nozzle section 4 and an enlarged debouchment section 5. The central funnel opening 6 is dimensioned in a manner such that the pertinent transducer and the transmission tube joined to it can be guided through said tunnel.

For the method of the invention it is furthermore necessary that the relatively long protective tube, with the exception of the reservoir segment 1 and the junction segment adjacent thereto can be slid by hand onto the outer surface of the nozzle section 4. For this purpose, the dimensioning of said nozzle section and the protective tube are matched to each other. This means that the minimum inside diameter of the intermediate segment 2, which is $\phi = 18$ mm in the exemplary embodiment portrayed, is to some extent larger than the outside diameter of the nozzle section 4 of the fitting funnel. The result of the manual operation referred to above is portrayed diagrammatically in FIG. 3. The feed segment 3 is, under these circumstances, splayed out around the rim of the debouchment section 5 of the fitting funnel, the other section of the protective tube being situated in a gathered condition around the nozzle section 4. When the assembly of protective tube and fitting funnel is brought to the condition outlined above, the freely protecting reservoir segment ! can be filled with transmission gel. For this purpose, use may be made of a conventional hypodermic syringe and a narrow dosaging hose line connected thereto. A predetermined quantity, for example, 1 cm$^3$, of transmission gel is thus injected via the fitting funnel into the reservoir 1 of the protective tube.

As the next step, the transducer and a section of the transmission tube adjacent thereto are guided through the central channel 6 of the fitting funnel until said transducer is situated in the interior of the reservoir segment 1 and is acoustically coupled with the transmission gel introduced into the latter. The transmission tube is then held in place while the fitting funnel is moved over it in a direction moving away from the transducer, which, like the transmission tube remains in its place. During said movement, the section of the protective tube situated on the nozzle section is successively pulled off of said nozzle section. An instantaneous record of this unrolling operation is portrayed diagrammatically in FIG. 4.

The result can thus be achieved that the transducer and the transmission tube joined thereto are enclosed by the protective tube while only the transducer is in contact with transmission gel.

Via the debouchment section 5 of the fitting funnel, the assembly consisting of protective tube and fitting funnel can then be rigidly coupled to the operating case. For this purpose, the fact is beneficial that an end section of the protective tube is splayed out around the debouchment rim of the fitting funnel. With the succession of steps described above, a situation has arisen in which the transducer and transmission tube, enclosed by the protective tube can be introduced into the body of a patient to be examined.

After the examination has been completed and the transducer and transmission tube enclosed by the protective tube have been removed from the patient, the fitting funnel is decoupled from the operating case. After this, said fitting funnel and the protective tube attachment thereto can be removed from the transmission tube and the transducer. Finally, the protective tube is removed from the nozzle section and the debouchment section in order to be thrown away.

In principle, the cross sections of the protective tube and the fitting funnel may have a shape different from the circular shape such as, for example, an oval shape.

In view of the manufacturing technology, the intermediate segment of the protective tube is preferably shaped so as to extend somewhat conically as is evident from FIG. 1. For the sake of completeness, attention is drawn to the fact that the diameter dimensions portrayed in FIG. 1 indicate a pertinent inside diameter of the protective tube. The wall thickness of the protective tube is approx 0.25 mm. If an ultrasound transducer is used, the protective tube should obviously be transparent to ultrasound.

It is also possible to make use of a transducer, the working field of which extends from the head section of the reservoir.

The invention is also applicable to the field of endoscopy, as described in the U.S. Pat. No. 4,646,722.

I claim:

1. Method for fitting a flexible elongated thin-walled protective sheath including a sealed end section around an endoscopic device having an imaging head and an elongated transmission tube joined thereto for transmitting image signals originating from said imaging head, said elongated transmission tube being connected to an operating case having a conically-shaped sloping section towards said transmission tube comprising the steps of:
   a) sliding and gathering said protective sheath except said sealed end section onto a nozzle section of a fitting funnel including an enlarged conically-shaped end section;
   b) splaying an open end section of said protective sheath about said enlarged concically-shaped end section of said fitting funnel;
   c) coursing said imaging head and elongated transmission tube into said fitting funnel via said conically-shaped end section to a point where said imaging head is positioned in said sealed end section of said protective sheath;
   d) moving said fitting funnel over said transmission tube towards said operating case; and
   e) coupling said fitting funnel to said operating case by a detachable coupling.

2. The method as defined in claim 1 wherein said imaging head is an ultrasound transducer and prior to step c), injecting a transmission medium conductive of ultrasound transmission into said sealed end section of said protective sheath whereby said ultrasound transducer is acoustically coupled to said transmission medium.

3. A fitting assembly for a diagnostic assembly comprised of an imaging head, an elongated transmission tube and an operating case, which comprises:
   a fitting funnel including a nozzle section and a conically-shaped end section for receiving said imaging head;
   a protective sheath including an imaging head end receiving segment, an intermediate segment and an opened end segment opposite said imaging head end receiving segment, said protective sheath being dimensioned to fit over said fitting funnel except for said imaging head end receiving segment, said intermediate segment being of a length to be gathered over said nozzle section of said fitting funnel prior to positioning of said imaging head, said opened end segment cooperating in fitting relationship with said conically-shaped end section of said fitting funnel; and
   means for coupling said fitting funnel to said operating case.

4. The fitting assembly for a diagnostic assembly as defined in claim 3, wherein said means for coupling comprises a ring member formed on an inner surface portion of said conically-shaped end section of said fitting funnel.

5. The fitting assembly as defined in claim 3 or 4 wherein said intermediate section of said protective sheath is of a length to accommodate said elongated transmission tube with said opened end segment splayed over said conically-shaped end section of said fitting funnel.

6. The fitting assembly as defined in claim 3 or wherein said opened end segment of said protective sheath is larger in diameter than said nozzle segment thereof and wherein said diameter of said nozzle segment and said open end segment of said protective sheath is larger than said diameter of said nozzle section and said conically-shaped end section of said fitting funnel.

7. The fitting assembly as defined in claim 3 or wherein said imaging head end receiving segment is of smaller diameter than said intermediate segment of said protective sheath and said nozzle section of said fitting funnel.

* * * * *